United States Patent [19]
Torrie et al.

[11] Patent Number: 5,380,334
[45] Date of Patent: Jan. 10, 1995

[54] SOFT TISSUE ANCHORS AND SYSTEMS FOR IMPLANTATION

[75] Inventors: Paul A. Torrie, Marblehead; Gary P. Tallent, Gloucester, both of Mass.

[73] Assignee: Smith & Nephew Dyonics, Inc., Memphis, Tenn.

[21] Appl. No.: 58,631

[22] Filed: May 6, 1993

Related U.S. Application Data

[63] Continuation-in-part of Ser. No. 18,449, Feb. 17, 1993, abandoned.

[51] Int. Cl.$^6$ .............................................. A61B 19/00
[52] U.S. Cl. .................................... 606/104; 606/75
[58] Field of Search ................................ 606/72–75, 606/104; 411/49 S; 24/297

[56] References Cited

U.S. PATENT DOCUMENTS

| | | | |
|---|---|---|---|
| 4,590,928 | 5/1986 | Hunt et al. | 128/92 |
| 4,716,893 | 1/1988 | Fischer et al. | 128/92 |
| 4,834,752 | 5/1989 | Van Kampen | 623/13 |
| 4,851,005 | 7/1989 | Hunt et al. | 623/18 |
| 4,924,865 | 5/1990 | Bays et al. | 606/77 |
| 4,976,715 | 12/1990 | Bays et al. | 606/77 |
| 4,988,351 | 1/1991 | Paulos et al. | 606/75 |
| 5,013,316 | 5/1991 | Goble et al. | 606/72 |
| 5,037,422 | 8/1991 | Hayhurst et al. | 606/72 |
| 5,041,129 | 8/1991 | Hayhurst et al. | 606/232 |
| 5,046,513 | 9/1991 | Gatturna et al. | 128/898 |
| 5,084,050 | 1/1992 | Draenert | 606/77 |
| 5,085,661 | 2/1992 | Moss | 606/139 |
| 5,098,435 | 3/1992 | Stednitz et al. | 606/73 |
| 5,100,417 | 3/1992 | Cerier et al. | 606/139 |
| 5,102,421 | 4/1992 | Anspach, Jr. | 606/232 |
| 5,129,906 | 7/1992 | Ross et al. | 606/77 |
| 5,192,303 | 3/1993 | Gatturna et al. | 606/232 |
| 5,203,784 | 4/1993 | Ross et al. | 606/104 |
| 5,203,787 | 4/1993 | Noblitt et al. | 606/232 |
| 5,209,753 | 5/1993 | Biedermann et al. | 606/72 |
| 5,236,431 | 8/1993 | Gogolewski et al. | 606/72 |
| 5,236,445 | 8/1993 | Hayhurst et al. | 606/232 |
| 5,246,441 | 9/1993 | Ross et al. | 606/53 |
| 5,268,001 | 12/1993 | Nicholson et al. | 606/72 |

FOREIGN PATENT DOCUMENTS

| | | |
|---|---|---|
| 340159 | 4/1988 | European Pat. Off. . |
| 270704 | 6/1988 | European Pat. Off. . |
| 409364 | 7/1990 | European Pat. Off. . |
| 504915 | 9/1992 | European Pat. Off. . |
| 560249 | 9/1993 | European Pat. Off. . |
| 2084468 | 9/1981 | United Kingdom . |
| 2266246 | 10/1993 | United Kingdom . |

OTHER PUBLICATIONS

Undated publication from Arthrex, Inc. regarding Bone/Tissue Anchoring.
Nicholson, U.S. Ser. No. 07/765,445, filed Sep. 25, 1991, entitled "Bone Fastener".

*Primary Examiner*—Stephen C. Pellegrino
*Assistant Examiner*—Gary Jackson
*Attorney, Agent, or Firm*—Pravel Hewitt Kimball & Krieger

[57] ABSTRACT

Surgical kits for the implantation of soft tissue-to-bone anchors and expandable, preferably bioabsorbable, soft tissue anchors. The surgical kits include an embodiment with an outer tube with an expandable anchor releasably attached to its distal end, for guiding the anchor into a predrilled hole; an inner tube with an anchor expanding pin sized for expanding the anchor releasably held in its bore; and a pushrod for pushing the anchor pin into the anchor to expand it and wedge it in a hole. In an alternative embodiment, the anchor pin is attached to the distal end of a pushrod inserted into an outer tube. In one embodiment, the anchor is equipped with downward extending spikes on the underside of an enlarged head for gripping soft tissue and bending barbs to resist withdrawal of the anchor from bone. In another embodiment, the anchor's proximal end has no enlarged head but is equipped with sutures. In a further embodiment, the anchor's enlarged head is tilted at an angle to allow better engagement of spikes with soft tissue.

22 Claims, 6 Drawing Sheets

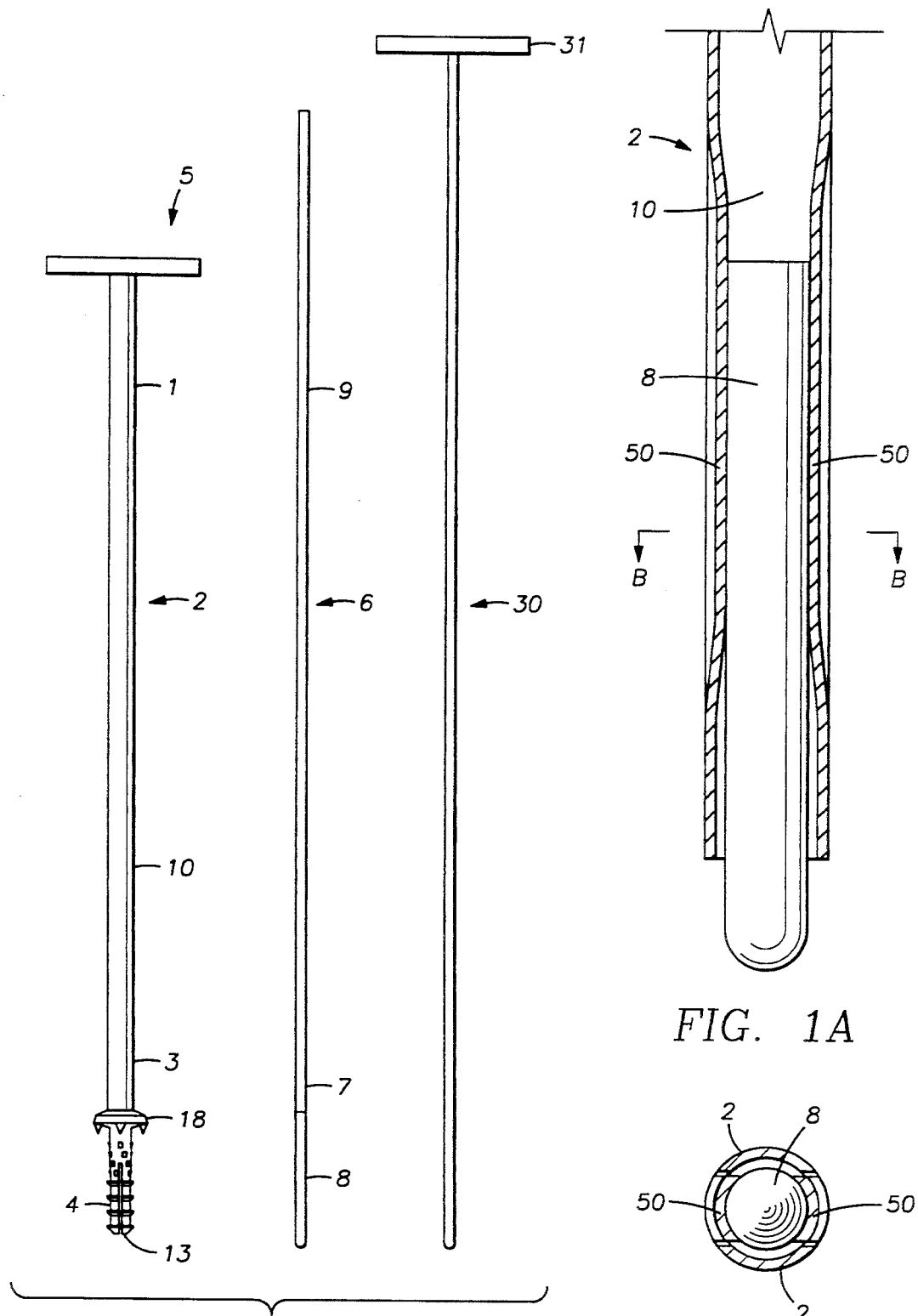
FIG. 1
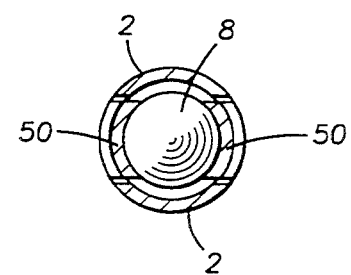
FIG. 1A
FIG. 1B

SOFT TISSUE ANCHORS AND SYSTEMS FOR IMPLANTATION

This application is a continuation-in-part of U.S. Ser. No. 08/018,449, filed on Feb. 17, 1993 now abandoned.

BACKGROUND OF THE INVENTION

1. Field of the Invention

The invention is of a system for implanting soft tissue anchors for holding soft tissue in place relative to bone. More particularly, the invention provides a system for readily implanting soft tissue anchors as well as soft tissue anchors that are equipped with structural features preventing their inadvertent withdrawal from bone holes.

2. Description of the Related Art

In the field of surgery it is sometimes necessary to perform operations to reattach soft tissue to bone. For example, U.S. Pat. No. 4,924,865 describes a repair tack designed for use in arthroscopic surgery to repair a torn meniscus in the knee. Reattachment of soft tissue to bone may also arise, for instance, when surgery is performed on a shoulder to remove or repair glenohumeral tissue.

Regardless of the circumstance, whenever bone must be reattached to tissue, it is desirable to have a fastener or "anchor" that will hold the tissue onto the bone at its point of reattachment, and that will allow the tissue to heal and naturally reattach itself to the bone. Thus, it is desirable that the soft tissue fixation element should not interfere with the healing process and should allow progressively heavier loads to be placed on both bone and soft tissue to encourage healing and development of attachment strength.

U.S. Pat. Nos. 4,590,928 and 4,851,005 disclose surgical implants that include an expandable stud and a pin for insertion into the stud to expand the stud. The stud and pin are both fabricated from biodegradable polymeric materials, and include carbon fibers aligned along their longitudinal axes. The stud body has an enlarged head at one end and, at the opposite end, its cylindrical surface is longitudinally split. Further, the stud has a cylindrical bore running throughout its length along its longitudinal axis. The pin is inserted into this bore thereby forcing the split distal ends radially outwards, to expand the stud body and lodge it firmly in a hole in bone. The stud and pin combination is used to connect a synthetic flexible cord for holding two bones together in a mammalian body.

Likewise, U.S. Pat. No. 4,834,752 is directed to a "tissue augmentation device" for repairing ligaments or tendons. The device includes at least one strap-like element (substitute tendon) formed of stable biocompatible material and a biodegradable element for connecting the strap-like element to bone. The biodegradable fasteners shown in FIGS. 2 and 4 of the '752 patent, include a pin having a longitudinal body with a head at one end, a longitudinal bore through the body, and slits at the distal end of the body producing longitudinal distal segments. A pin is insertible into the bore of the body for expanding the segments radially outward so that they will grip the sides of a hole in bone. The embodiment of FIG. 4 shows barbs extending downward from the undersurface of the head for engaging the strap-like element and holding it in place.

EPO Application No. 0 409 364 shows a conical-shaped implant for joining together bone fragments. The longitudinal body of the implant is supplied with a conical axial hole, and a pin for inserting into the hole to expand the body of the implant, and wedge it firmly in surrounding bone tissue. The implant is bioresorbable to eliminate the need for later surgical removal. The outer surface of the implant is equipped with barb-like projections, presumably for assisting in holding the implant in place in the bone hole.

U.S. Pat. Nos. 4,590,928 and 4,851,005, likewise show an expandable stud for attaching a flexible cord, of biocompatible fibers in a biocompatible matrix, to bone. The stud has a longitudinal body with a head a one end, a bore extending along its longitudinal axis, and is split at its distal end to form separate legs so that when a pin is placed within the bore, it expands the legs radially outward to wedge the stud firmly in a hole.

What is yet needed is a surgical implantation kit that allows easy, accurate implantation of soft tissue anchors at desired bone-soft tissue contact points. The implanted anchors should grip soft tissue against the bone to promote rapid attachment and should decrease its gripping strength over time to gradually reduce stress shielding there by shifting stress loads to the soft tissue-bone interface so that the interface strengthens as it heals. Further, the anchors should be relatively small, to avoid drilling large holes in bone and soft tissue that increase healing time, but at the same time should resist being pulled out of the bone hole by applied forces.

SUMMARY OF THE INVENTION

The invention provides a surgical kit for the implantation of soft tissue-to-bone anchors, and expandable soft tissue-to-bone anchor studs.

In one embodiment, the invention surgical implantation kit includes a hollow outer tube with a distal end to which is releasably or threadingly attached a soft tissue anchor, with its longitudinal axis aligned with the longitudinal axis of the outer tube. The soft tissue anchor has a bore along its longitudinal axis, through which a guiding K-wire or other guiding means may be freely drawn, and into which an anchor expanding pin may be wedged to expand the anchor body and lodge it securely in a hole in bone. The surgical implantation kit also includes a longitudinal inner tube, sized to fit within the hollow bore of the outer tube. An anchor pin, for expanding the anchor body, is frictionally held at the distal end of the inner tube. A pushrod, sized to fit within the inner tube, is supplied with means for gripping and applying leverage to force the anchor pin from the inner tube into the bore of the soft tissue anchor stud. This is achieved by nesting the inner tube into the outer tube. The inner tube has the anchor pin at its distal end and the pushrod inserted into its proximal end. Applying force to the pushrod forces the anchor pin into the bore of the anchor stud to wedge the stud in the bone hole.

In order to insert an anchor stud using the surgical implantation kit of the invention, soft tissue to be connected to bone is drawn into position across the surface of the bone to which it must be attached. This may be done by grasping or skewering the soft tissue with the tip of the K-wire. A suitable location for tacking the soft tissue to the bone is then selected. A hole is drilled through the tissue and into the bone at the selected location to the desired depth, using a cannulated drill with a K-wire, or other guide means, inserted into the drill cannula. When the hole has been drilled to a predetermined depth, the drill is removed but the K-wire or other guide means is retained in place. The soft tissue anchor and the outer tube of the invention implantation apparatus are then placed around the implanted K-wire. In this manner, the anchor is guided into place in the drilled hole. When the anchor is in position, the K-wire or other guide means is removed. In one embodiment, the inner tube is then placed inside the outer tube and the anchor-expanding pin at the distal end of the inner tube is guided and pushed into the anchor stud by depressing the pushrod which is nested in the inner tube, causing the anchor to expand so that its sides tightly grip the sides of the hole. When the anchor pin has been fully inserted, the outer tube can be released, sheared from, or threadingly disengaged from the inserted anchor.

In another embodiment, the surgical implantation kit includes an outer tube with an anchor stud releasably held at its distal end and a cannulated plunger designed to fit within the inner tube. The anchor pin is releasably held on the distal end of the plunger and is pushed into the anchor stud when the plunger is depressed. To insert an anchor stud, a hole is drilled as described above and the K-wire is passed through the cannulation of the anchor stud, into the outer tube, and then through the cannulation of the plunger. Thus, the anchor stud is guided into the hole. When the anchor stud is in place in the bone hole and the K-wire is removed, the plunger is depressed to guide and force the anchor pin into the communicating bore of the anchor stud. When the pin has entered and expanded the anchor stud, the outer tube containing the pushrod can be disconnected from the anchor stud and the plunger can be released from the anchor pin.

The invention also provides specific soft tissue anchor stud designs that are not easily removed from the hole in the bone. Further, the soft tissue anchors are preferably comprised of a bioabsorbable polymeric composition designed so that, as the bone and tissue heal together, the anchors will gradually bioabsorb thereby transferring stress to the attachment point and facilitating healing while minimizing stress shielding.

In particular, in one embodiment the invention soft tissue anchor stud comprises an elongated body portion having distal and proximal ends. The proximal end is supplied with an enlarged head having an underside equipped with downwardly extending spikes for gripping soft tissue. The underside surface of the head is preferably also angled at an angle $\beta$ to the horizontal so that soft tissue is gripped between the spikes and the angled undersurface which form a pinch point for gripping soft tissue.

Typically, the soft tissue anchor is inserted into a hole which is drilled at an angle of up to 30° from the perpendicular in the bone. Thus, under ordinary circumstances, when the bone hole is angled, only the spikes on one side of the anchor will tightly engage soft tissue. The downwardly extending spikes on the other side may only lightly engage tissue.

In a second embodiment, the anchor stud does not have an enlarged head but instead is equipped with sutures attached to or embedded in the anchor body that can be used to affix soft tissue to an anchor wedged in a bone hole.

In an alternative embodiment, the anchor stud has an enlarged head tilted at an angle $\gamma$, approximating the angle to the perpendicular at which a hole is drilled into the bone. Thus, the tilt angle of the head permits downwardly extending spikes located on the underside of the head to engage soft tissue and hold the soft tissue firmly, but without inducing necrosis, between the underside of the head and the bone surface. This tilt-headed anchor stud is also expandable in that it is supplied with a longitudinal bore into which an expanding pin may be inserted to radially outwardly expand expandable legs of the anchor stud.

A longitudinal bore extends along the longitudinal axis of the invention's soft tissue anchors passing through their distal end. At the distal end, the soft tissue anchors have several legs, extending parallel with the longitudinal axis and radially outwardly expandable when an anchor pin is inserted into the longitudinal bores of the anchors. This radial outward spreading of the legs forces the legs against the sides of a bone hole and wedges the anchor studs securely in the hole.

To further assist in wedging the invention's anchor stud in place, the outside surface of the legs are provided with barb-like projections for engaging bone. These bone-engaging barbs counteract forces acting along the longitudinal axis of the anchor to withdraw the anchor from the bone hole. Further, on the upper or proximal portion of the outer surface of the anchor body, there are provided a series of "bending barbs" each placed so that they do not impede insertion of the anchor, and do not damage the bone tissue by broaching away bone that other bending barbs must later engage. These bending barbs resist forces acting at an angle to the longitudinal axis of the anchor body to remove the anchor from the bone. Specifically, these angled forces cause the anchor to bend slightly in the hole thereby forcing the bending barbs to engage bone tissue and thereby preventing the withdrawal of the anchor from the bone hole.

The invention anchor stud and pin for expanding the anchor stud may be made of any biocompatible polymer. Suitable nonbioabsorbable biocompatible polymers include ultra high molecular weight polyethylene (UHMWPE) and the like. Bioabsorbable polymers are preferred for certain applications and include polylactic acid, polyglycolic acid, copolymers thereof, and the like.

The invention provides surgical soft tissue anchor implantation kits that are easy to use for the implantation of any expandable soft tissue anchors in any surgical operation where it is desired to anchor soft tissue or soft tissue substitute, such as a synthetic ligament, to bone. Further, the invention provide specific types of soft tissue anchors that are bioabsorbable, expandable, and that resist withdrawal forces acting on the anchors.

BRIEF DESCRIPTION OF THE DRAWINGS

A better understanding of the present invention can be obtained when the following "detailed description of the preferred embodiments" is considered in conjunction with the following drawings which are not to scale and in which significant features have been exaggerated to show detail.

FIG. 1 is a schematic diagram of an embodiment of the invention system for the implantation of an expandable soft tissue anchor.

FIG. 1A is a schematic enlarged view of a distal portion of the inner tube of FIG. 1 showing the anchor pin held in place.

FIG. 1B is a cross-sectional view of FIG. 1A taken at B—B.

DETAILED DESCRIPTION OF THE PREFERRED EMBODIMENTS

Figure 2:
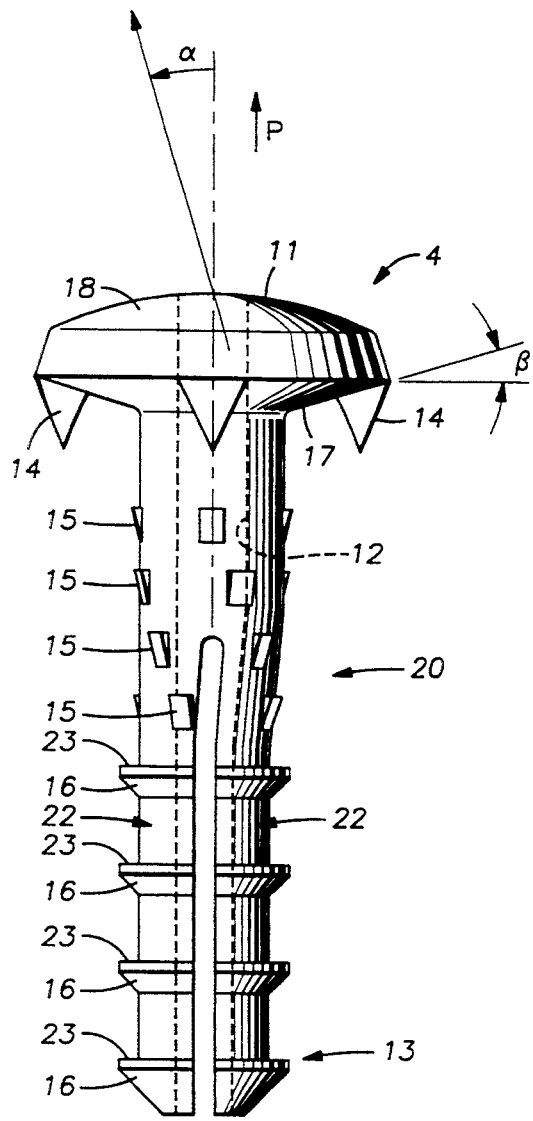
FIG. 2 is a schematic diagram of an embodiment of the invention soft tissue anchor with the left hand side in the "expanded position" and right hand side in the non-expanded, or "insertion position."

The preferred embodiment of the invention surgical kit for implantation of a soft tissue anchor may better be understood with reference to FIG. 1. A soft tissue anchor 4 is attached to the distal end 3 of an outer tube 2, which also has a proximal end 1. The outer tube is hollow and has a longitudinal bore 10 extending along the entire length of the outer tube 2. The distal end of the outer tube 3 is releasably or threadingly connected to the upper surface of the head 11 of soft tissue anchor 4. An anchor bore 12, coextensive with and communicating with outer tube bore 10, extends longitudinally through soft tissue anchor 4 from its proximal extremity to its distal extremity. The distal end 13 of anchor stud 4 includes at least two separate legs 22, each outwardly expandable when an anchor pin, sized to fit snugly within the bore of the soft tissue anchor, is positioned within the bore of soft tissue anchor 4.

An inner tube 6, sized to fit within the bore 10 of outer tube 2, is equipped with a releasably held anchor pin 8, as shown in FIGS. 1A and 1B. With reference to FIG. 1A, a segment of inner tube 6 is slit horizontally at four places thereby producing segments 50. These segments are resilient and two opposing segments can be depressed inward towards the longitudinal axis of bore 9 of inner tube 6. Thus, the depressed segments 50 create a pinch point of sufficient clamping action to hold anchor pin 8 in place. When the anchor stud 4, releasably held at the distal end 3 of outer tube 2 has been implanted in the bone hole, then inner tube 6 is inserted into the bore 10 of outer tube 2 and pushrod 30 is inserted into the bore 9 of inner tube 6. Pushrod 30 is then depressed by pushing on leveraging means 31 while holding gripping means 5. This depressing of pushrod 30 releases anchor pin 8 from the pinch point of segments 50 and guides the pin down the bore 9 to the communicating bore in anchor stud 4 into which the anchor pin 8 is then forced by pushrod 30 thereby expanding legs 22 of stud 4 radially outward to hold the stud in place. When the anchor pin 8 has been inserted into the soft tissue anchor, then the outer tube can be released from or threadingly disengaged from the implanted soft tissue anchor. The release of the outer tube 2 from the anchor stud 4 may be achieved by shearing a connection of predetermined strength between the two devices, by unscrewing one from the other, or by other means.

Figures 7, 7A:
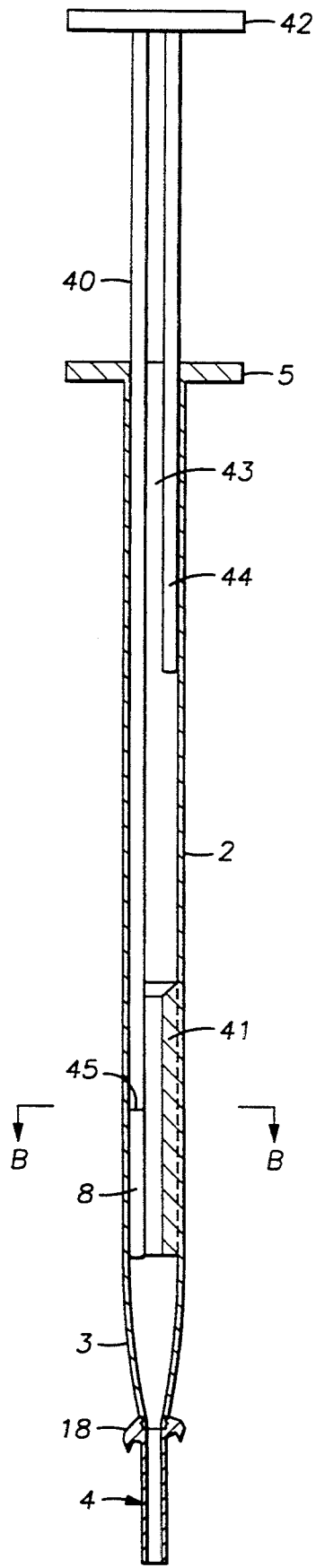
FIG. 7 is a schematic diagram of an embodiment of a system for implantation of an expandable soft tissue anchor.
FIG. 7A is a cross-section along B—B of FIG. 7 showing the anchor expanding pin held by the outer tube by friction.

In an alternative embodiment, the surgical implantation kit does not require an inner tube. With reference to FIG. 7, showing this alternative embodiment, a plunger 40 is desirably permanently engaged within an outer tube 2. The outer tube 2 has an anchor stud 4 releasably engaged at its distal end 3. This releasable engagement may be achieved by screw threads cooperating between distal end 3 and the head 8 of anchor stud 4. Alternatively, the anchor stud may be releasably held by friction or may be engineered for attachment with the distal end of the tube with a predesigned weakening at the point of attachment so that the distal end 3 may be separated cleanly from the head 8 upon application of an appropriate amount of force. In this embodiment, plunger 40 has an anchor pin 8 releasably attached to its distal end. As shown, the distal end of the plunger pushes against pin 8 at point 45. See FIG. 7A. Further, plunger 40 is preferably fabricated and assembled so that the surgical implantation unit presented to the user has plunger 40 already inserted into outer tube 2, as shown in FIG. 7. A segment of the plunger 40 is extended so that, in the plunger depressed position point 45 is below the head 18 of the anchor 4. In order to use this embodiment of the implantation kit, a hole is drilled in the usual manner and the K-wire used for guiding insertion of the anchor stud is inserted through the anchor stud 4, into the cooperating bore of outer tube 2, and then into the bore 43 of plunger 40. When the anchor stud 4 has been positioned within the bone hole, the K-wire is removed and plunger 40 is depressed using depression means 42 and outer tube gripping means 5. Upon depression of plunger 40, anchor pin 8 is forced into the bore of anchor stud 4, expanding the anchor stud into place in the bone hole. At this point, cooperating stop means 44 on plunger 40 contacts and is engaged by stop means 41 of outer tube 2. Preferably, the distal end 3 of outer tube 2 is internally shaped to guide anchor pin 8 into position in the bore of anchor stud 4 when pushrod 40 is depressed.

The above-described surgical systems for implantation of soft tissue anchors can be used with any design of soft tissue anchor that is supplied with a bore for expanding the body of the anchor to wedge the anchor securely in a bone hole. The anchors may be fabricated from bioabsorbable or nonbioabsorbable polymeric compositions, and other biocompatible materials. The soft tissue anchor may, for instance, be supplied with a smooth cylindrical body or shaft, or may have barbs extending from the shaft, as shown in the invention soft tissue anchor of FIG. 2. Further, the soft tissue anchors useful with the invention's surgical implantation kit may or may not include sharp-edged barbs downwardly extending from the undersurface of the head of the anchor for gripping soft tissue. Indeed, useful anchors need not have an enlarged head.

Figure 3:
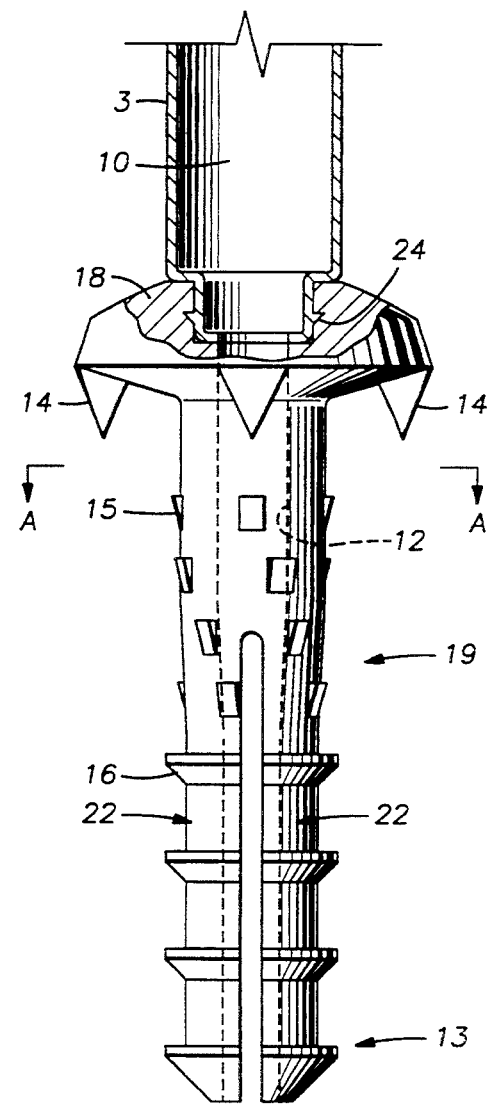
FIG. 3 is a schematic diagram of an embodiment of the invention soft tissue anchor showing its attachment to the distal end of an outer tube.
Figure 3A:
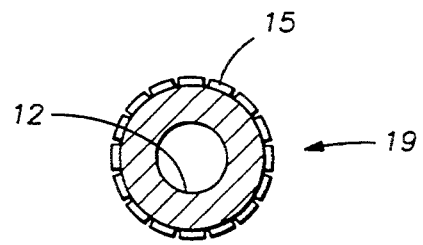
FIG. 3A is a schematic diagram of a cross section taken of FIG. 3 at A—A.
Figure 4:
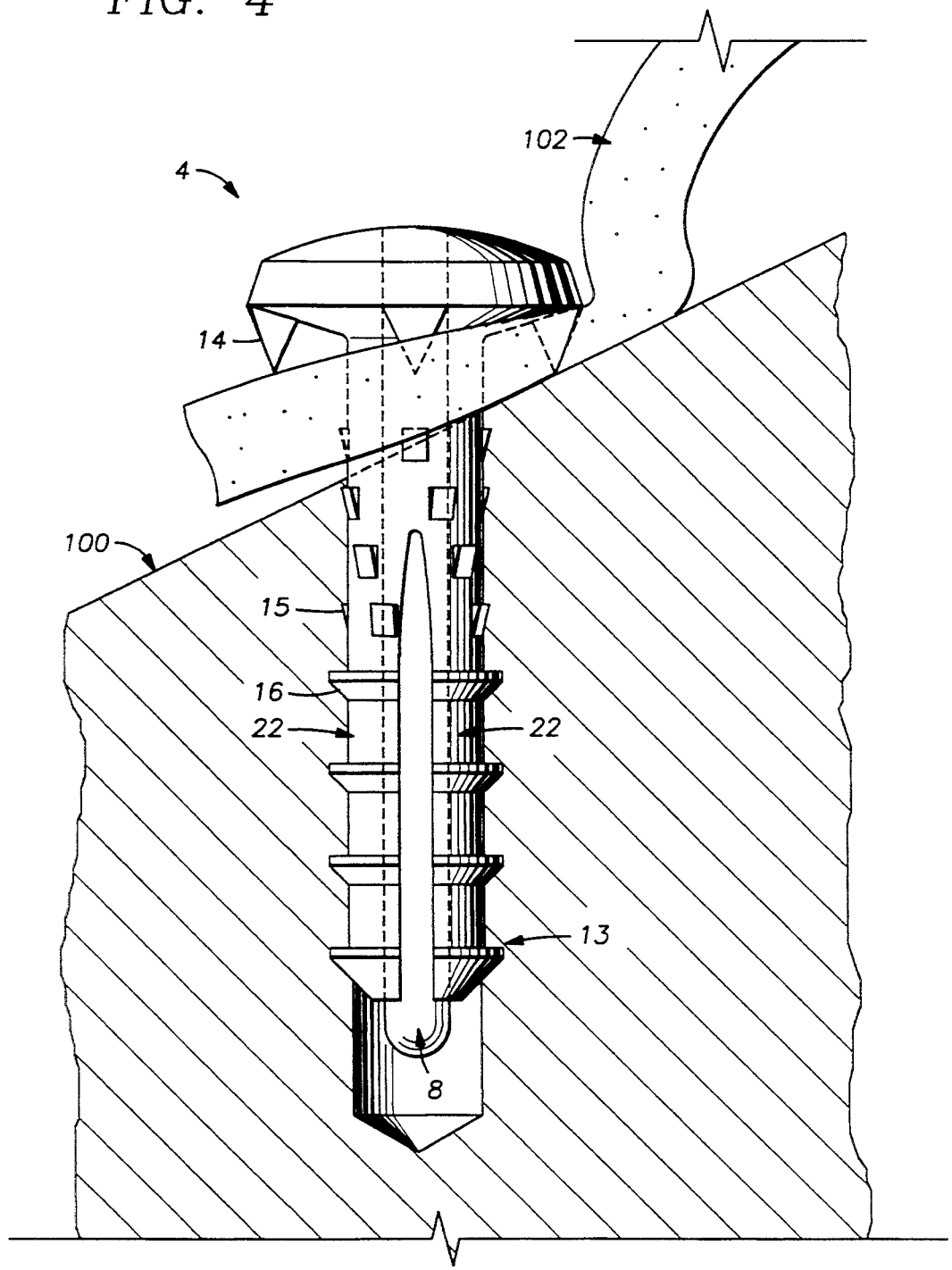
FIG. 4 is a schematic diagram showing an embodiment of the invention soft tissue anchor implanted in bone and gripping soft tissue.

An embodiment of the invention's soft tissue anchors is shown in FIGS. 2, 3, and 3A. From FIG. 2, the soft tissue anchor 4 has an enlarged head 18, with an upper surface 11, and an undersurface 17. The undersurface 17 is at an angle $\beta$ to the horizontal. This has significant implications because the anchor is normally placed in a hole drilled at an angle about $\beta$ (about 15°) to the horizontal. Consequently, only about one half of the undersurface of the head 18 will intimately and tightly contact soft tissue when the anchor is in place, as can be seen from FIG. 4 where bone is represented by 100 and soft tissue 102. The other half of the head undersurface will extend above the soft tissue or will only marginally contact the tissue. Soft tissue engaging barbs 14 extend downwardly from surface 17 and are sized to approximate the thickness of the soft tissue to allow such firm embedment in the tissue as is needed without inducing necrosis of the soft tissue. The soft tissue anchor has an elongate body 20 extending downwardly from the head 18. The body has a proximal end 19 and a distal end 13. A bore 12 extends along the longitudinal axis of the body 20 and passes through the head 18. The distal end of the anchor body 20 is divided into separate legs 22. In FIG. 2, the right hand side leg is shown in a "non-expanded position" before an expanding pin is placed within the bore 12. On the other hand, the left hand side leg 22 is shown in the "expanded position" after an anchor expanding pin has been forced into the bore 12.

The anchor is supplied with barbs 16 shaped to allow ease of insertion but having sharp upper edges 23 to bite into the bone and resist withdrawal, when a withdrawal force is applied along the axis of the anchor in the direction P. Further, the proximal half 19 of the outer surface of the soft tissue anchor is supplied with "bending barbs" 15, each positioned on the anchor circumference so as not to broach bone away from the next succeeding barb. These sharp, low profile barbs 15 are designed to engage trabecular bone structure when the anchor is bent slightly. This bending usually occurs when forces are applied to pull the anchor from its implanted position in the bone hole. Typically, the angle of applied force $\alpha$ is about 15° to about 45° off the perpendicular axis of the anchor stud. When force is applied at the angle $\alpha$, then the anchor, because it is flexible, tends to bend slightly. When this bending occurs, the "bending barbs" 15 engage trabecular bone structure and oppose withdrawal of the anchor 4 from its position in the hole. The positioning of the barbs 15 around the circumference or outer surface of the proximal portion 19 of the soft tissue anchor 4 can most easily be seen with reference to FIG. 3A.

Figure 5:
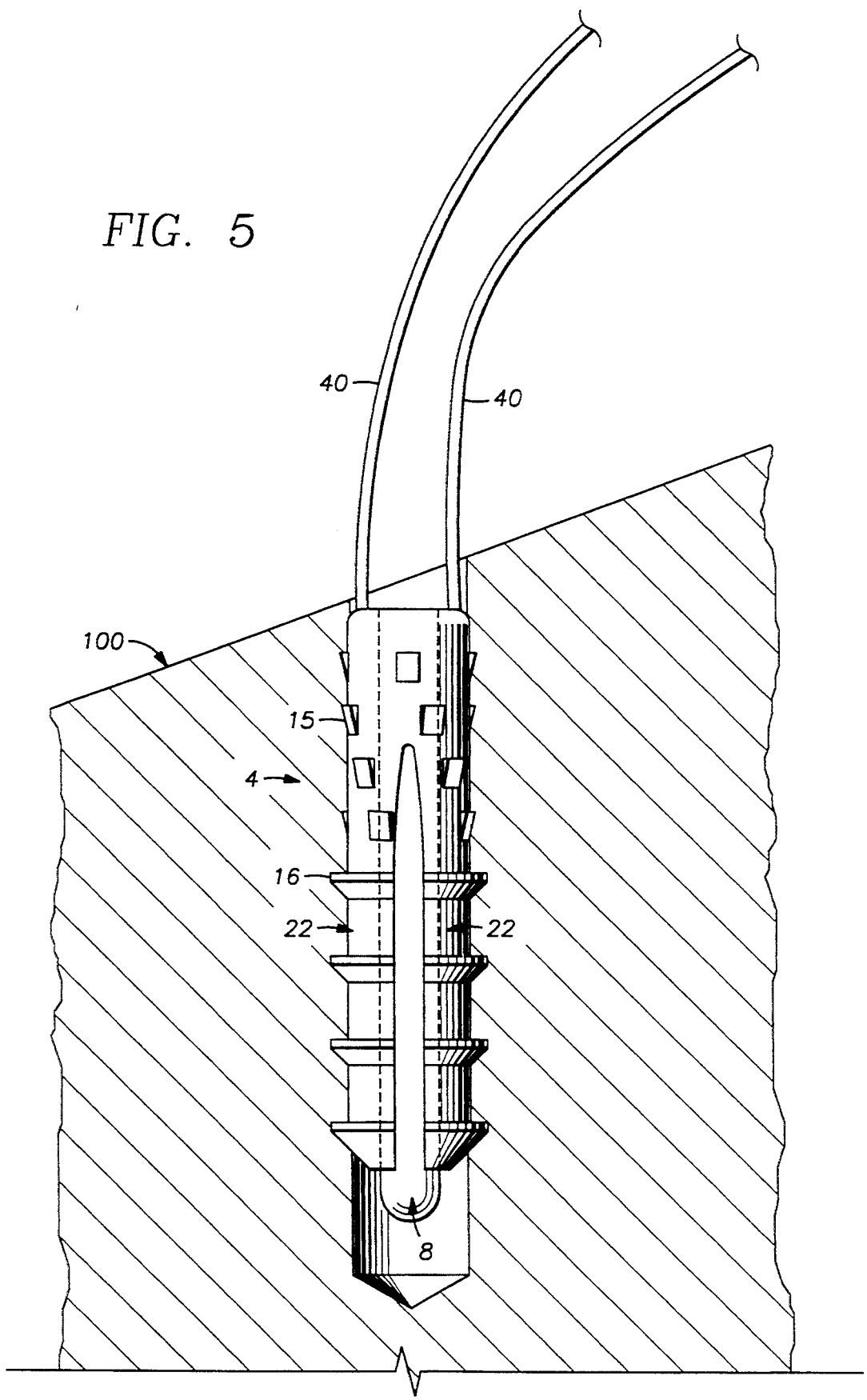
FIG. 5 is a schematic diagram of an embodiment of the soft tissue anchor stud implanted in bone.

An alternative embodiment of the invention soft tissue anchors is shown in FIG. 5. In this embodiment, the soft tissue anchor does not include an enlarged head with an angled undersurface and downwardly extending spikes. Instead, sutures 40 are embedded or fixedly attached to the expandable anchor. These sutures 40 may be used to affix soft tissue to bone 100 or for other purposes, as needed. In this embodiment, the anchors include barbs 16 to counteract forces withdrawing the anchor from its implanted position, and bending barbs 15 to resist withdrawing forces applied at an angle to the longitudinal axis of the anchor stud.

Figure 6:
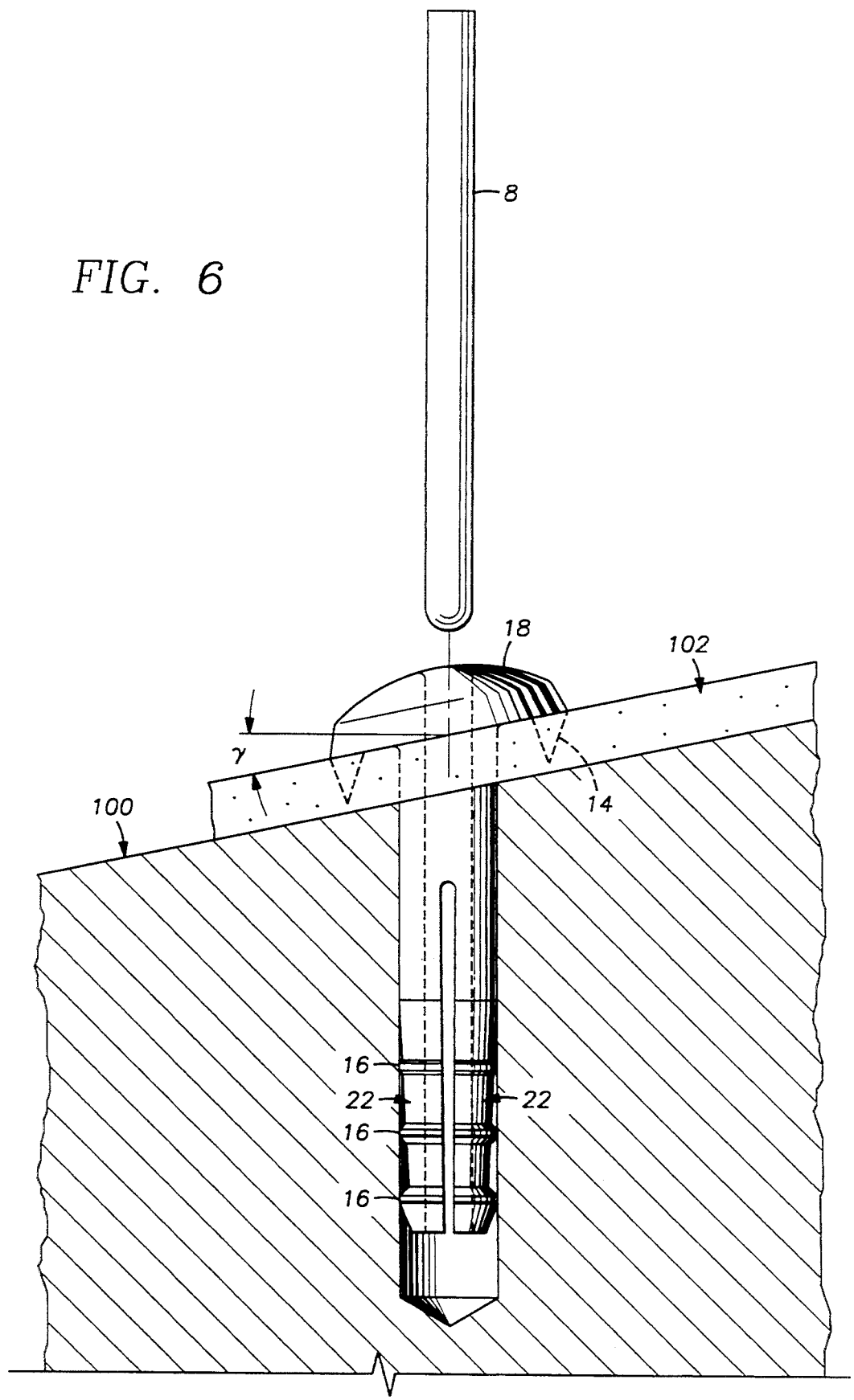
FIG. 6 is a schematic depiction of an anchor stud with a tilted head and legs radially outwardly expandable.

A further alternative embodiment of the invention soft tissue anchors is shown in FIG. 6. In this embodiment, the head 8 is tilted at an angle $\gamma$ to the horizontal so that when the anchor is implanted, the undersurface of the head fits flushly against soft tissue 102 while downwardly extending spikes 14 engage body tissue. In this manner, unlike the typical untilted head shown in FIG. 4, the soft tissue anchor is more effective in holding soft tissue in place. Whereas the soft tissue anchor of FIG. 6 is supplied with barbs 16 on outwardly expandable legs 22, the soft tissue anchor may also be further equipped with bending barbs, in a manner similar to that shown for the embodiment of FIG. 4. The angle $\gamma$ is from about 10° to about 30°, preferably about 20°.

The invention soft tissue anchors can be used in conjunction with the soft tissue anchor surgical implantation kit described above. FIG. 3 shows the connection between the distal end 3 of outer tube 2 with head 18 of anchor 4. In this particular embodiment, the outer tube distal end 3 is insert molded into the head 18 and is held in place by gripping means 24 interacting with a groove or cooperating means in head 18. The anchor pin 8, sized to the approximate length of the anchor body 20 and head 18, is inserted into bore 12 from the head of the anchor and is forced to the distal end of the anchor 13, thereby expanding legs 22 radially outward to grip the sides of the bone hole.

The method for implanting soft tissue anchors using the invention's surgical implantation devices requires firstly positioning the soft tissue over the segment of bone to which it must be attached. With K-wire locked into the cannulated drill and extending about ¼ inch beyond the drill tip, the soft tissue is skewered and moved into position over the bone. The drill is then used to drill a hole to a predetermined depth in the bone. Thereafter, the drill is removed with the K-wire, or other guide means, remaining in place in the hole so that the free end is inserted into the distal end 13 of anchor 4 and into the bore 10 of tube 2. This allows guiding of the anchor 4 through the soft tissue and into the bone hole. When the shaft 20 of the anchor is firmly placed in the hole, then in the embodiment of FIG. 1, the inner tube 6 is inserted into outer tube 2 and pushrod 30 inserted into inner tube 6. The pushrod 30 is pushed with gripping and leverage means 31 until the appropriately sized anchor pin 8 enters the bore 12 in anchor 4 thereby radially outwardly expanding legs 22 so that gripping barbs 16 and edges 23 tightly engage the sides of the bone hole. Once this has been achieved, outer tube 6 can be released from the anchor 4, leaving the latter in place in the bone hole, tightly gripping the soft tissue. The methods of using other embodiments of the implantation kit are discussed fully above.

The foregoing disclosure and description of the invention are illustrative and explanatory thereof, and various changes in the size, shape, materials, as well as in the details of the illustration may be made without departing from the spirit of the invention as disclosed above and claimed below.

What is claimed is:

1. A surgical kit for implanting a soft tissue anchor, the kit comprising:
   (i) an outer tube having an elongate body with distal and proximal ends, and a longitudinal bore along the length of the body for receiving an inner tube;
   (ii) an anchor stud having a longitudinal axis, the anchor stud releasably affixed to the distal end of the outer tube, the anchor stud comprising a bore along the anchor stud longitudinal axis, said bore in communication with the bore in the outer tube, the anchor stud having at least two radially-outward expandable legs;
   (iii) an inner tube having an elongate body with distal and proximal ends, the inner tube body sized for insertion into the longitudinal bore in the outer tube;
   (iv) an anchor stud-expanding pin held in the bore of the inner tube, the pin sized for expanding the legs of the anchor stud radially outward to grip walls of a hole in bone; and
   (v) a pushrod sized for insertion into the inner tube and equipped with means for leveraging the pushrod to force the anchor stud-expanding pin into the bore of the anchor stud for expanding the legs outwardly to grip bone.

2. The surgical kit of claim 1, wherein the anchor stud and anchor stud expanding pin comprise a bioabsorbable polymeric composition.

3. The surgical kit of claim 2, wherein the anchor stud and expanding pin are of a bioabsorbable polymeric composition selected from the group consisting of polylactic acid, polyglycolic acid, and copolymers thereof.

4. The surgical kit of claim 1, wherein the anchor stud is releasably attached to the outer tube by screw threads.

5. The surgical kit of claim 1, wherein the anchor comprises:
a radially-outward expandable anchor stud, the stud having proximal and distal ends and an elongate body with an outer surface and a longitudinal axis; the stud further comprising:
(a) a longitudinal bore extending along the stud's longitudinal axis for receiving a stud-expanding pin;
(b) at least two radially-outward expandable legs on the distal end of the stud for gripping the sides of a bone hole;
(c) a plurality of bending barbs on a proximal half of the outer surface of the elongate stud body for gripping bone and resisting forces, at an angle to the stud's longitudinal axis, withdrawing the stud from a bone hole; and
(d) gripping barbs on a distal half of the outer surface of the elongate stud body for holding the stud in a bone hole.

6. The surgical kit of claim 5, wherein the anchor stud and stud-expanding pin comprise a bioabsorbable polymeric composition.

7. The surgical kit of claim 5, wherein the anchor stud further comprises an enlarged head at the proximal end thereof, the enlarged head comprising an undersurface at an angle (90°+$\beta$), measured as the angle between the undersurface of the head and the longitudinal axis of the anchor stud, said undersurface comprising spikes downwardly extending therefrom for engaging soft tissue.

8. The surgical kit of claim 5, wherein the anchor stud further comprises sutures at the proximal end.

9. The surgical kit of claim 5, wherein the anchor stud further comprises an enlarged head tilted at an angle $\gamma$ to the horizontal at the proximal end thereof, the enlarged head comprising an undersurface with spikes downwardly extending therefrom for engaging soft tissue.

10. A surgical kit for implanting soft tissue anchors, the kit comprising:
(i) an outer tube having an elongate body with distal and proximal ends, a longitudinal bore along the length of the body for receiving a pushrod;
(ii) an anchor stud having a longitudinal axis, the anchor stud releasably affixed to the distal end of the outer tube, the anchor stud comprising a bore along the longitudinal axis in communication with the bore in the outer tube, the anchor stud having at least two radially-outward expandable legs; and
(iii) a pushrod sized for insertion into the outer tube, the pushrod equipped with (a) an anchor stud-expanding pin releasably attached at its distal end, and (b) means for leveraging the pushrod into the bore of the outer tube at its proximal end, the anchor stud-expanding pin being sized for fitting into the bore of the anchor stud for expanding the legs outwardly.

11. The surgical kit of claim 10, wherein the anchor stud and anchor stud-expanding pin comprise a bioabsorbable polymeric composition.

12. The surgical kit of claim 11, wherein the anchor stud and expanding pin are of a bioabsorbable polymeric composition selected from the group consisting of polylactic acid, polyglycolic acid, and copolymers thereof.

13. The surgical kit of claim 10, wherein the anchor stud is releasably attached to the outer tube by screw threads.

14. The surgical kit of claim 10, wherein the anchor stud comprises:
a radially-outward expandable anchor stud, the stud having proximal and distal ends and an elongate body with an outer surface and a longitudinal axis; the stud further comprising:
(a) a longitudinal bore extending along the longitudinal axis for receiving a stud-expanding pin;
(b) at least two radially-outward expandable legs on the distal end of the stud for gripping the sides of a bone hole;
(c) a plurality of bending barbs on a proximal half of the outer surface of the elongate stud body for gripping bone and resisting forces, at an angle to the stud's longitudinal axis, withdrawing the stud from a bone hole; and
(d) gripping barbs on a distal half of the outer surface of the elongate stud body for holding the stud in a bone hole.

15. The surgical kit of claim 14, wherein the anchor stud further comprises an enlarged head, the enlarged head comprising an undersurface at an angle $\beta$ to the horizontal and downwardly extending spikes for engaging soft tissue.

16. The surgical kit of claim 15, wherein the anchor stud and expanding pin comprise a bioabsorbable polymeric composition.

17. The surgical kit of claim 14, wherein the anchor stud further comprises sutures inserted at the proximal end of the anchor stud.

18. The surgical kit of claim 17, wherein the anchor stud and expanding pin comprise a bioabsorbable polymeric composition.

19. The surgical kit of claim 14, wherein the anchor stud further comprises an enlarged head tilted at an angle $\gamma$ to the horizontal, the enlarged head comprising an undersurface with downwardly extending spikes for engaging soft tissue.

20. The surgical kit of claim 1, wherein the stud further comprises an enlarged head at the proximal end of the stud, the enlarged head being tilted at an angle $\gamma$ to the horizontal, the enlarged head comprising an undersurface having downwardly extending spikes for engaging soft tissue.

21. The surgical kit of claim 20 further comprising from about eight to about sixteen bending barbs.

22. The surgical kit of claim 20 further comprising about four gripping barbs.

* * * * *